(12) United States Patent
Quint et al.

(10) Patent No.: US 9,033,918 B2
(45) Date of Patent: May 19, 2015

(54) POLYAMIDE/POLYVINYLPYRROLIDONE (PA/PVP) POLYMER MIXTURE AS CATHETER MATERIAL

(75) Inventors: Bodo Quint, Oberglatt (CH); Matthias Wesselmann, Rudlingen (CH); Laura Sager, Zurich (CH)

(73) Assignee: BIOTRONIK AG, Buelach (CH)

( * ) Notice: Subject to any disclaimer, the term of this patent is extended or adjusted under 35 U.S.C. 154(b) by 180 days.

(21) Appl. No.: 13/995,679

(22) PCT Filed: Nov. 23, 2011

(86) PCT No.: PCT/EP2011/070814
§ 371 (c)(1),
(2), (4) Date: Jun. 19, 2013

(87) PCT Pub. No.: WO2012/084390
PCT Pub. Date: Jun. 28, 2012

(65) Prior Publication Data
US 2013/0324922 A1     Dec. 5, 2013

Related U.S. Application Data

(60) Provisional application No. 61/425,254, filed on Dec. 21, 2010.

(51) Int. Cl.
*A61M 29/00* (2006.01)
*A61L 29/12* (2006.01)
*A61L 29/04* (2006.01)
*A61M 25/10* (2013.01)

(52) U.S. Cl.
CPC .......... *A61L 29/126* (2013.01); *Y10T 428/1352* (2015.01); *Y10T 428/139* (2015.01); *Y10T 428/1397* (2015.01); *Y10T 428/1393* (2015.01); *A61L 29/049* (2013.01); *A61M 25/1029* (2013.01)

(58) Field of Classification Search
CPC ............... A61L 29/126; A61L 29/049; A61M 25/1029; Y10T 428/1352; Y10T 428/139; Y10T 428/1393; Y10T 428/1397
USPC ....................................... 604/96.01
See application file for complete search history.

(56) References Cited

FOREIGN PATENT DOCUMENTS

| | | |
|---|---|---|
| DE | 199 33 279 A1 | 3/2001 |
| EP | 0 697 219 A2 | 2/1996 |
| WO | WO 2006/065905 | 6/2006 |

OTHER PUBLICATIONS

Int'l. Search Report issued in Int'l. App. No. PCT/EP2011/070814, mailed Aug. 2, 2012 (Translation Not Available).

*Primary Examiner* — Michael C Miggins
(74) *Attorney, Agent, or Firm* — Greer, Burns & Crain, Ltd.

(57) ABSTRACT

An embodiment of the present invention relates to a catheter comprising a dilatable balloon, characterized in that the primary balloon wall is produced from a material that comprises or consists of a polyamide/polyvinylpyrrolidone (PA/PVP) polymer mixture.

19 Claims, No Drawings

POLYAMIDE/POLYVINYLPYRROLIDONE (PA/PVP) POLYMER MIXTURE AS CATHETER MATERIAL

CROSS REFERENCE TO RELATED APPLICATIONS

This application is a U.S. National Phase under 35 U.S.C. §371 of International Application No. PCT/EP2011/070814, filed Nov. 23, 2011, which application is a non-provisional of U.S. provisional Application Ser. No. 61/425,254.

TECHNICAL FIELD

The present invention relates to a catheter. Some embodiments comprise a dilatable balloon, characterized in that the primary balloon wall is produced from a material that comprises or consists entirely of a polyamide/polyvinylpyrrolidone (PA/PVP) polymer mixture.

BACKGROUND

Angioplasty, including percutaneous transluminal angioplasty (PTA) or percutaneous transluminal coronary angioplasty (PTCA), is a method for widening or reopening narrowed or obstructed blood vessels (usually arteries, at times also veins). A common method used in angioplasty is balloon dilation.

Balloon dilation within the context of angioplasty is understood in interventional radiology, cardiology, and angiology as a method for dilating pathologically narrowed blood vessels by way of a balloon catheter, a vessel catheter having a balloon attached thereon. A balloon may be inflated slowly under high pressure (e.g., 6-20 bar) only after it has been navigated to the narrowed site. In this way, occlusions created primarily by atherosclerotic changes (sclerosis of the blood vessels) are expanded so that they no longer, or less severely, impair the blood flow.

To this end, the balloon catheters are generally inserted to the site of the stenosis (occlusion) from the groin using a guide wire and guide catheter and are inflated with pressure. In this way, the stenosis is eliminated and surgery is avoided.

Aside from this, catheters comprising a deflatable balloon are also used for the placement of stents. To this end, in the region of the deflatable balloon the catheter carries a stent, which can be placed into the vessel, after the desired site in the blood vessel has been reached, by deflating the balloon.

Modern methods in the field of plastics processing allow such balloons to be designed and continuously developed so as to individually adapt the quality to the needs of the patients. The flexibility of the balloons and the pressure resistance therefore are important factors in this process.

Polyamides and PEBA materials used in catheter production are typically based on the polyamide 12 (PA12) base structure. This polyamide is characterized by high strength and toughness, low water absorption and changes in properties associated therewith, and by good availability of the raw materials. PA12 is a common catheter material and, for reasons of good deformability, is popular as a base material for catheter balloons. The practical application for balloon components requires high pressure resistance, a low wall thickness, and high softness of the cones.

In order to improve the properties of the balloon when using a particular material, the orientation and crystallinity properties of the material are deliberately influenced. The elasticity, and hence the orientation, of the polymer can be improved by using additives, which increase the sliding qualities of the molecule chains against each other and/or reduce the crystallization of the polymer before deformation, for example by using suitable softeners and/or solvents.

PA12-based systems typically have a glass transition temperature of approximately 50° C. Temperatures above 50° C. are used to blow mold the balloon components. In order to impress a shape memory in these components, mold constraint and conditioning above or around the glass transition temperature are used, for example for folding and fixing the stent. In principle, heating the blow-molded components in the range of the glass transition temperature and above enables a relaxation of the stresses impressed by the plastic shaping. The relaxation causes hysteresis, for example, between the first and further, subsequent pressure stresses of the balloon component. As a competing effect, the crystallization of the polymer further progresses starting at 50° C.

Since polyamides during radiation sterilization typically suffer a loss of mechanical strength, and temperatures that are considerably higher than the glass transition temperature result in severe dimensional changes, EtO (ethylene oxide) sterilization has become established as a typical sterilization method for balloon catheters. The EtO sterilization processes are conducted under thermal conditions around 50° C. If the balloon catheter is EtO-sterilized, this thermal stress, in the presence of moisture, constitutes the absolute minimum of the relaxation of PA12-based components during the production of the catheter. In general, the balloon component is conditioned using thermal methods so as to obtain reproducible dimensions already after sterilization, which then no longer change considerably, even as a result of simulated aging and storage. However, this also means that the balloon compliance of the first inflation differs substantially from all subsequent inflation processes and is more drastic during the initial inflation. This effect is also associated with an increase in the diameter of the balloon component. Since the compliance of these components is determined during the first inflation, subsequent inflations of the balloon result in a certain systematic overdilation of the vessels. The increase in the diameter of the balloons, as the number of inflations and the inflation intensity increase, is therefore a safety-relevant quality criterion.

Less advantageous usage properties of PA12 balloons, which may be caused by harder balloon cones, for example, can be reduced, for example in terms of the material, by using a softer material—this being generally PEBA types or polymer mixtures of PA12 comprising such PEBA types. In general, however, the glass transition temperature of PA12 remains unchanged.

The viscoelastic properties of PA12 are even more pronounced with these PETA types. Starting at temperatures of approximately 50° C., these viscoelastic properties result in shrinkage, which leads to a distinct change of the balloon diameter between the first and any subsequent pressure inflations. In this way, this material optimization means that compromises are made in terms of the precision of the dilation behavior. The precision of the dilation is generally reduced as a result.

SUMMARY

It is the object of the present invention to mitigate or prevent one or more disadvantages of the prior art.

Embodiments of the present invention achieve this object by providing a catheter comprising a dilatable balloon, characterized in that the primary balloon wall is produced from a material that comprises or consists entirely of a polyamide/polyvinylpyrrolidone (PA/PVP) polymer mixture.

By adding polyvinylpyrrolidone (PVP), preferably as an oligomeric to macromolecular addition to polyamides, a polymer mixture or blend is achieved, which can be used to produce the primary balloon wall of the dilatable balloon of a catheter and components of the shaft of invention embodiments. The balloon or the components obtained in this way are characterized by a broadening of the deformation boundaries and by delayed crystallization, increased elasticity and generally a decreased modulus of elasticity, and in an increase in the glass transition temperature in the dry state of the sample. This range of properties is of great benefit in terms of technology, because an increase in elasticity broadens the deformation boundaries during the blow molding process and because a greater reinforcement effect can be achieved by increasing the orientation of the polymers. With a design according to an invention embodiment, the decrease in the modulus of elasticity of the material is thus compensated for by a gain in orientation of the polymer. This results in a considerable improvement of the usage properties of the balloon.

The delayed crystallization after extrusion achieves improved and more tolerant shaping boundaries, which is particularly advantageous for the balloon deformation and the process stability thereof. For example, during shaping it is possible to achieve smaller necks, or regions of the shaped cylindrical part of the balloon that are stretched higher. In this way, balloons having more flexible cones are obtained, because the elasticity is increased and the crystallization tendency during the thermal treatment is reduced. Because of the softer cones of the balloon, for example, improved rewrapping after the inflation of the balloon component is achieved. Broadening the deformation boundaries creates the opportunity to achieve greater stretching for the cylindrical region of the balloon, and hence counteract a reduction in the modulus of elasticity, and optionally increased compliance of the balloon component, because greater orientation of the stretch-formed component can be achieved.

The crystallization of the blend is primarily temporally delayed and can thus still be increased up to a maximum using suitable process engineering. In this case, it has been discovered, for example, starting at a concentration of approximately 3% weight addition, under crystallization conditions, that the PA12 polymer matrix, at molecular weights that correspond to the commercial PVP type K30, diffuses the PVP addition into boundary regions of the component, and under certain circumstances in precipitated phases. Under unfavorable process conditions, balloon components composed of a blend of PA12/PVP may tend to form punctiformly failing regions, referred to as "pin holes", after crystallization. When developing such components, a molecular weight-dependent limit concentration should therefore be observed. In the case of "polymer hinges", which require a very robust breakage behavior of the polymer, very pronounced micro-cracking based on this phase separation of the polymer, which is observed, for example for PA12, at concentrations as low as 3% weight addition, due to blending with the commercial PVP type K90, can certainly be advantageous. In this way, for example, catheters can be made, which are based on folding or locally bending elements and nonetheless have a very low tendency to break at the movement sites with maximum deformation.

In the dry state, the balloons have an elevated glass transition temperature and thus tend to very low relaxation during dry storage and dry thermal treatment. Despite the increased moisture absorption capacity, no abnormally increased relaxation was observed on balloon components in EtO sterilization cycles. After forming and orienting the polymer mixture, PVP is enriched at the phase boundary. While polyamides typically exhibit low reactivity and wettability on the surface, the presence of PVP on the surface has an adhesion-promoting, wetting effect and a hydrophilizing effect. For example, after shaping balloon components in a water bath, complete wetting of the surface with water is observed and lower slipperiness is noticed in terms of haptics. Because PVP allows both lipophilic and polar interactions and, by nature, constitutes a vinyl polymer, balloon assemblies composed of PA/PVP polymer mixtures can be glued very well using acrylates, contrary to pure polyamides. These compounds have proven to be more resistant to aging and delamination. Even without an added coating, the balloon surface exhibits better adhesion to polar and nonpolar physically adhering coatings, such as active ingredient-releasing cover layers. Since the surface is wetted significantly better by aqueous systems, it is easier to fill hoses or cavities without bubbles. In medical technology, this is essential in many areas—for example in oxygenators—and it also extremely helpful, and depending on the application, of safety-relevant interest, for catheters having particularly large and/or long balloons. Dilations in the region of the left atrium, adjoining pulmonary nerves, the left ventricle, and in the region of the aortic valve must be carried out with relatively large balloon components due to the dimensions. These should generally be prepared bubble-free, because, in the event of failure, they may release gas bubbles and can cause micro-embolisms in the cranial and coronary tissues.

In keeping with the explanations provided above with respect to the changed mechanical properties, and the interface phenomena that were observed, the present invention comprises not only catheters having a dilatable balloon, but also other catheter applications with an advantageous implementation of the PA/PVP blend.

The invention essentially relates to a catheter comprising a dilatable balloon. This may encompass catheters that are suited to apply a stent and comprise a dilatable balloon for this purpose. However, it also encompasses catheters comprising dilatable balloons that may be used directly for treatment, for example within the context of balloon dilation for widening vascular stenoses. In principle, any known catheter system may be used for the catheter according to the invention, and preferably any catheter system comprising a dilatable balloon.

One invention embodiment in particular relates to a catheter having an inner shaft, to the distal end of which a dilatable balloon is fastened, which in a non-expanded, deflated state is at least partially seated against an outer surface of the inner shaft. In addition to an inner shaft and the dilatable balloon, catheters of the intended type may also comprise an outer shaft, which extends at least up to a proximal end of the balloon and is connected thereto in a fluid-tight manner. Between the inner and outer shafts of the catheter, typically a fluid line is provided, which extends in a longitudinal direction of the catheter from the proximal end to the inside of the balloon and which is obtained, for example, by designing the inside diameter of the outer shaft larger than an outside diameter of the inner shaft.

On the inside of the inner shaft, a hollow space that is enclosed by the inner shaft and extends in the longitudinal direction of the inner shaft is provided as the lumen. This lumen is used, for example, to receive a stylet or a guide wire. The catheter and guide wire are then designed, for example, such that the guide wire can exit at the distal tip of the catheter and can be controlled from the proximal end. The guide wire, for example, is deflected using control means such that it can be easily introduced, even into branching blood vessels. The balloon catheter can then be advanced along the guide wire.

Regardless of the type of the catheter, and particularly in terms of the design of the guide means, the catheters according to the invention comprise this dilatable balloon at the distal end. During insertion of the catheter, the balloon is compressed and seated closely against the inner shaft of the catheter. By inflating the balloon with a fluid, it can be expanded or dilated. This expansion of the balloon is carried out as soon as the region of the catheter comprising the dilatable balloon has been navigated to the intended position. By expanding the balloon, a stent may be applied or a surface of the balloon is placed against a vascular wall. This is done, for example, for the purpose of widening vascular constrictions (stenoses) by way of the balloon of the catheter.

The catheter according to some invention embodiments is characterized in that the primary balloon wall of the dilatable balloon is composed of a material comprising or consisting of a PA/PVA polymer mixture. The primary balloon wall shall be understood as the wall that encloses the lumen of the balloon and thereby forms the balloon. The primary balloon wall forms the basis of the balloon or the wall thereof, to which later optionally additional materials and/or coatings may be applied. The primary balloon wall expressly does not comprise those additional or subsequently added coatings that may be applied, or have been applied, to the inner and/or outer surfaces of the primary balloon wall.

The PA/PVP polymer mixture denotes a polymer blend comprising or consisting of the two polymer types of polyamide (PA) and polyvinylpyrrolidone (PVP). A polymer mixture or polymer blend shall be understood as a physical mixture of the polymers and is present as a macroscopically homogeneous mixture of the different polymers. No chemical reaction takes place between the different polymers. In the literature, there are discussions that a complex may be formed between polyamide bonds of the PA and the pyrrole ring of the PVP. Polymer mixtures or blends are produced by mechanically mixing melted polymers, yielding a homogeneous material. In particular, polymer mixtures can be obtained by adding one polymer in solid or liquid form to the melt of the other polymer and melting it therewith. The different polymer chains remain mixed as the mixed melt is cooled, and it is believed that, when mixed with sufficient intensity and when the dosage is sufficiently low, physical mixing of the two polymers is achieved, which is lastingly maintained.

The PA/PVP polymer mixture comprises a polyamide content and a polyvinylpyrrolidone content and may optionally comprises further components, such as solvents and/or softeners.

Given the wetting effect, an interesting variant may also be the use as a processing aid for dispersing fillers or reinforcement agents. For example, it is possible to exfoliate phyllosilicates (clays) in an aqueous solution in the presence of PVP. Using a spray drying process, it is possible to produce a pourable powder, which can be fed to the compounding process by way of a gravimetrically metering rocking conveyer. Because the increase in viscosity of the clays in an aqueous solution is significant and may create process engineering-related problems, the exfoliation of the clay in a hydrous mixture, such as an alcohol-water mixture, may be employed as a method variant. In this way, it is possible to structurally reinforce the polymer into a phyllosilicate-reinforced material (nanocomposite) and advantageously influence the crystallinity thereof by way of excess PVP, which can be dissolved in the polyamide-based polymer matrix. The phyllosilicate content for this purpose should be less than 7% (by weight) and approximately 1-5% (by weight) of PVP. Other values are within the scope of the invention.

The weight percentages of the polyamide and polyvinylpyrrolidone portions together preferably amount to 100% by weight of the PA/PVP polymer mixture in man but not all, invention embodiments.

The weight percent of the PVP in the PA/PVP polymer mixture in many invention embodiments is <10% by weight relative to the total weight of the PA/PVP polymer mixture. The weight percent of the polyvinylpyrrolidone content in the PA/PVP polymer mixture can be 0.01 to 7% by weight, relative to the total weight of the PA/PVP polymer mixture, 0.5 to 5% by weight being preferred, and 1 to 3% by weight being also preferred. In the PA/PVP polymer mixture, polyvinylpyrrolidone is preferably used with an average molecular weight of oligomer compounds up to compounds having an average molecular weight of 2,500,000 g/mol. The polyvinylpyrrolidone content of the PA/PVP polymer mixture useful in many invention embodiments may comprise or consist entirely of a polyvinylpyrrolidone having a K-value of 20 to 100, PVP having a K-value (K-value according to Fikentscher) of 30 to 90; or PVP having a K-value of 30, 60, or 90; or other K-values. It has been discovered to be advantageous to deliberately reduce the molecular weight of PVP by using suitable process engineering, wherein preferably high-molecular components are to be decomposed. This reduction in the molecular weight can be achieved, for example, by the action of intensive mechanical shearing (using an Ultra-Turrax dissolver for example, or in other ways) and by intensive ultrasonic action on dissolved PVP.

The weight percent of the polyamide in the PA/PVP polymer mixture in many embodiments is >10% by weight relative to the total weight of the PA/PVP polymer mixture. The polyamide content of the PA/PVP polymer mixture may comprise only a certain polyamide or a mixture of different polyamides. The polyamide may be a homopolymer or a copolymer. The polyamide content of the PA/PVP polymer mixture in many embodiments preferably comprises or consists entirely of a polyamide that is selected from the group consisting of PA5, PA6, PA7, PA8, PA9, PA10, PA11, PA12, PA13, PA14 and/or PA15, or a copolymer comprising at least one monomer of the aforementioned type, preferably PA6, PA7, PA8, PA9, PA10, PA11 and/or PA12, or a copolymer comprising at least one monomer of the aforementioned type, wherein it is particularly preferred when the polymer is a PA12.

As an alternative, for example, some embodiments use polyurethanes or peptides in the polymer mixtures according to the invention, rather than polyamides.

As an alternative to PVP, some embodiments use PVP copolymers in the polymer mixtures according to the invention (such as the product family available under the Luvitec trade name).

PVP reduces the hydrogen bond formation of the amide bond, which is presumably linked to a complex formation with the PVP. In this way, the property spectrum of both aliphatic and aromatic polyamide types can be changed.

The PA/PVP polymer mixture of one example catheter according to the invention can be produced and/or compounded using known methods. The PA/PVP polymer mixture is preferably produced by compounding, because in this way both gentle and adjusted shear for mixing can be achieved. Weight-controlled metering of the individual components is the state of the art for this method. The polymer mixture is preferably produced in a twin screw compounder using gravimetric metering for granules, and the PVP is produced in a powdery consistency. The dried, finely dispersed PVP is preferably fed, for example, by way of a rocking conveyor to a PA melt. The use of a inert atmosphere and vacuum degasing of the plasticized and mixed belt prior to extrusion is advantageous.

In the catheter according to some invention embodiments, in addition to the balloon, other components of the catheter may be produced from a material that comprises or consists of a PA/PVP polymer mixture.

The catheter according to invention embodiments may comprise, at least on parts of the outer surface of the dilatable balloon, a drug-eluting coating and/or cavity filling. The coating may also cover the entire outer surface of the balloon. A coating as defined by the invention denotes an application of the constituents of the coating onto at least some regions of the outer surface of the dilatable balloon of the catheter. The surface of the balloon denotes the outer surface, which can typically brought in contact, or is brought in contact, with the vascular wall during clinical use. The coating preferably covers the entire outer surface of the balloon, but may cover only portions in some embodiments. A layer thickness preferably ranges from 1 nm to 100 μm, with the range of 300 nm to 50 μm being another preferred example. The coating can be directly applied to the balloon surface. The processing can be carried out according to standard coating methods. It is possible to produce single-layer or multi-layer system (such as so-called base coat, drug coat, or drug comprising top coat layers). The coating may be directly applied onto the balloon body, or additional layers may be provided in between. As an alternative, or in addition, the catheter may comprise a cavity filling. The cavity is generally located on the outer surface of the dilatable balloon. Methods for coating catheters and for applying cavity fillings onto catheters are known to the person skilled in the art.

The present invention also relates to a method for producing the balloon of the catheter according to the invention, wherein the characteristic step of the method is the selection of the temperature, optionally in combination with the selection of the pressure, at which the shaping of the balloon takes place. The remaining steps of the method are consistent with known methods for producing balloons for catheters from polyamides, and notably PA12 or Pebax, and for the sake of brevity will not be described in detail here.

In some methods according to the invention, the shaping of a balloon from a PA/PVP polymer mixture is carried out at a temperature of ≥50° C., and preferably at a temperature of ≥80° C. The balloon shaping is generally carried out in a water bath or by way of a stretch blow molding process.

The invention also relates to the use of a material comprising or consisting of the aforementioned PA/PVP polymer mixture for producing catheters, and notably balloon catheters, preferably for the production of a dilatable balloon of a catheter.

DETAILED DESCRIPTION

Various aspects of invention embodiments will be explained in more detail hereinafter based on exemplary embodiments.

Embodiment

The PA/PVP polymer mixture is produced in a twin screw compounder using gravimetric metering. The polyamide was preconditioned in a recirculating dryer using routine measures. The PVP was previously dried over night in a vacuum drying chamber at 120° C. and dried at a pressure of <50 mbar.

In a first experiment, a twin screw compounder from Coperion having a screw diameter of 20 mm, L/D>40, gravimetrically controlled granules feeding and a gravimetric vibrating chute for dosing the powdery PVP into the PA melt was employed.

Two different PVP types, K30 and K90 from Bayer, and two gravimetric metering stages of 3% by weight and 6% by weight PVP, in each case relative to the total weight of the PA/PVP polymer mixture, were blended. The process temperature was adjusted to a temperature profile with at a maximum of 220° C.

The compounded melt was quenched in a water bath and fed to the strand pelletizer. These granules are subjected to more intensive drying than is common for pure polyamides of the same type because the water absorption capacity is considerably higher. After drying, the tube extrusion process is carried out, which differs only minimally from the typical extrusion conditions of polyamides. Experience has shown, however, that temperatures >220° C. should be avoided. After the extrusion into tubes, all test materials showed the ability of being shaped into balloons, if necessary using slightly modified process temperatures.

The mechanical properties of the compounded tubes resulted for both PVP types in similar properties with respect to the maximum elongation at fracture and tensile value. However, the visual impression of stretched samples is considerably different depending on the PVP type. Under the selected conditions, the K90 type indicated the formation of microcrack structures (crazes) by exhibiting white unbonded zones. The hoses of the K30 type, however, remained completely transparent. When the K30 type was used under these test conditions, the molecular weight and concentration were selected in a suitable fashion, and in this way complete physical dissolution of the PVP in the polyamide matrix was achieved.

For the balloon shaping, which was carried out in a water bath, the conditioning temperature had to be raised significantly, as compared to the unmodified polyamide. Typically, polyamides are blown at approximately 80° C. and pressures of about 40 bar with the process technology what was employed. The balloons composed of the PA/PVP polymer mixtures are blown at a temperature of approximately 95° C. and a pressure of approximately 40 bar.

The shaped PA/PVP balloons developed very suddenly, while the pure polyamide balloons according to the prior art were shaped less abruptly. The freshly demolded balloons from the water batch exhibited a slightly "slippery" behavior as compared to pure polyamide balloons.

The hoses produced from the PA/PVP polymer mixture can be shaped at higher radial stretching rates than pure polyamide balloons. The process yielded balloons having very flexible and thin cones. The PA/PVP balloons frequently contained pin holes. This is an indication that the compounding may be carried out under more aggressive conditions than was implemented up until now, and where applicable, the concentration of PVP may be reduced further. The frequency of pin holes is increased by an added tempering process. The frequency of the pin holes and the slippery behavior of the PA/PVP balloons after demolding from the water bath process allow the conclusion that, at high temperatures, the PA/PVP polymer mixture continues to tend to crystallize and restructure the polymer matrix, and PVP is displaced from the crystallizing regions of the polymer. It can be assumed that, during the crystallization process of PA12, PVP portions are removed from the amorphous matrix, or displaced from amorphous regions of the matrix. This observation indirectly confirms the effectiveness of this additive in maintaining the polyamide hose preferably in an amorphous state after extrusion so as to achieve broadened deformation boundaries of the polymer for the shaping process, and the desired effect of making a stronger and more dimensionally stable component possible due to the crystallization of the oriented polymer at elevated temperatures.

Blends comprising nylon 12 (Grilamid L25) and 6% by weight PVP (K30 Bayer) yielded balloons having shape diameters of 7.0 mm. The PA/PVP balloons had double wall thicknesses around 50 μm and increased diameters of 7.21 mm to 7.56 mm at 6 to 12 bar. Burst pressure levels of approximately 13-14 bar were achieved. This indicates a pressure resistance between PA12 and Pebax 7033, wherein interestingly the compliance remained considerably below that of Pebax balloons produced under comparable conditions.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. A catheter comprising a dilatable balloon, characterized in that a primary balloon wall is produced from a material that comprises polyamide/polyvinylpyrrolidone (PA/PVP) polymer mixture.

2. The catheter according to claim 1, wherein the PA/PVP polymer mixture comprises a polyamide content and a polyvinylpyrrolidone content, with the weight percentages of the polyamide and polyvinylpyrrolidone contents together totaling substantially 100%.

3. The catheter according to claim 1, wherein the weight percent of the polyvinylpyrrolidone content in the PA/PVP polymer mixture is 0.01 to 7% by weight.

4. A catheter according to claim 1, wherein the polyamide content of the PA/PVP polymer mixture comprises a polyamide that is selected from PA5 to PA15.

5. A catheter according to claim 1, wherein the polyvinylpyrrolidone content of the PA/PVP polymer mixture comprises a polyvinylpyrrolidone having an average molecular weight of 2,500 to 2,500,000 g/mol.

6. A catheter according claim 1, wherein the polyvinylpyrrolidone content of the PA/PVP polymer mixture comprises polyvinylpyrrolidone having a K-value of 20 to 100.

7. A catheter according to claim 1, and further comprising at least one further component produced from a material comprising or a PA/PVP polymer mixture.

8. A catheter according to claim 1, wherein the dilatable balloon comprises a coating or cavity filling on the outer surface of the primary balloon wall.

9. A catheter according to claim 1, wherein the catheter has a stent.

10. The catheter according to claim 1 wherein the primary balloon wall consists entirely of a polyamide/polyvinylpyrrolidone (PA/PVP) polymer mixture.

11. The catheter according to claim 1, wherein the weight percent of the polyvinylpyrrolidone content in the PA/PVP polymer mixture is 1 to 3% by weight.

12. The catheter according to claim 1, wherein the polyamide content of the PA/PVP polymer mixture is PA12.

13. The catheter according claim 1, wherein the polyvinylpyrrolidone content of the PA/PVP polymer mixture comprises a polyvinylpyrrolidone having a K-value selected from 30, 60 and 90.

14. A catheter according claim 1, wherein the polyvinylpyrrolidone content of the PA/PVP polymer mixture consists entirely of a polyvinylpyrrolidone having a K-value of 30 to 90.

15. A catheter according to claim 1, wherein the polyvinylpyrrolidone content of the PA/PVP polymer mixture consists entirely of polyvinylpyrrolidone having an average molecular weight of 2,500 to 2,500,000 g/mol.

16. A method for producing the dilatable balloon of a catheter according to claim 1, characterized in that the balloon shaping is carried out at a temperature of ≥50° C.

17. The method according to claim 16, wherein the balloon shaping is carried out at a temperature of ≥90° C. in a water bath.

18. Use of a material comprising or consisting of a PA/PVP polymer mixture for producing catheters, and notably balloon catheters, preferably for the production of a dilatable balloon of a catheter.

19. A catheter comprising a dilatable balloon having a wall that comprises a polyamide/polyvinylpyrrolidone (PA/PVP) polymer mixture, the weight percent of the polyvinylpyrrolidone content in the PA/PVP polymer mixture being 0.5 to 5% and the polyvinylpyrrolidone having an average molecular weight of 2,500 to 2,500,000 g/mol., the polyvinylpyrrolidone has a K-value of 30 to 90, the polyamide content of the PA/PVP polymer mixture comprises a polyamide that is selected from PA6 to PA12.

* * * * *